US012573034B2

(12) United States Patent　　　(10) Patent No.:　US 12,573,034 B2
Takahashi　　　　　　　　　　　　(45) Date of Patent:　　Mar. 10, 2026

(54) IMAGE PROCESSING APPARATUS, IMAGE PROCESSING METHOD AND PROGRAM, AND IMAGE PROCESSING SYSTEM

(71) Applicant: FUJIFILM Corporation, Tokyo (JP)

(72) Inventor: Azuma Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 460 days.

(21) Appl. No.: 18/168,569

(22) Filed: Feb. 14, 2023

(65) Prior Publication Data

US 2023/0196574 A1　　Jun. 22, 2023

Related U.S. Application Data

(63) Continuation of application No. PCT/JP2021/027869, filed on Jul. 28, 2021.

(30) Foreign Application Priority Data

Sep. 4, 2020　(JP) ................................. 2020-148709

(51) Int. Cl.
　　*G06K 9/00*　　　(2022.01)
　　*G06T 7/00*　　　(2017.01)
　　　　　　(Continued)

(52) U.S. Cl.
　　CPC ............ *G06T 7/0012* (2013.01); *G06V 10/44* (2022.01); *G06V 10/761* (2022.01); *G16H 30/20* (2018.01);
　　　　　　(Continued)

(58) Field of Classification Search
　　None
　　See application file for complete search history.

(56) References Cited

U.S. PATENT DOCUMENTS 9,852,269 B2　12/2017　Sakagawa et al.
10,297,352 B2　5/2019　Sakagawa et al.
(Continued)

FOREIGN PATENT DOCUMENTS

JP　　　H05101122　　　4/1993
JP　　　2007279942　　　10/2007
(Continued)

OTHER PUBLICATIONS

"International Search Report (Form PCT/ISA/210) of PCT/JP2021/027869" mailed on Sep. 21, 2021, with English translation thereof, pp. 1-5.
(Continued)

*Primary Examiner* — Wei Wen Yang
(74) *Attorney, Agent, or Firm* — JCIPRNET

(57) ABSTRACT

Provided are an image processing apparatus, an image processing method and program, and an image processing system that improve diagnostic accuracy by prompting processing requests more easily and without omission. The above object is achieved by the image processing apparatus, the image processing method and program, and the image processing system configured to acquire image features of a medical image of an examination target, acquire a reference case and a diagnostic log based on the image features, determine a recommended process for the medical image of the examination target based on the acquired reference case and diagnostic log, and present the recommended process.

10 Claims, 3 Drawing Sheets

(51) Int. Cl.

| | |
|---|---|
| *G06V 10/44* | (2022.01) |
| *G06V 10/74* | (2022.01) |
| *G16H 30/20* | (2018.01) |
| *G16H 50/20* | (2018.01) |
| *G16H 50/70* | (2018.01) |

(52) U.S. Cl.
CPC ............. *G16H 50/20* (2018.01); *G16H 50/70* (2018.01); *G06T 2207/30096* (2013.01)

(56) References Cited

U.S. PATENT DOCUMENTS

| | | | |
|---|---|---|---|
| 11,423,537 B2 | 8/2022 | Matsuki et al. | |
| 2011/0099032 A1 | 4/2011 | Miyasa et al. | |
| 2020/0242762 A1 | 7/2020 | Matsuki et al. | |
| 2021/0158525 A1* | 5/2021 | Iwase .................. | A61B 3/0025 |
| 2022/0358651 A1 | 11/2022 | Matsuki et al. | |

FOREIGN PATENT DOCUMENTS

| | | | | |
|---|---|---|---|---|
| JP | 2007287027 | 11/2007 | | |
| JP | 2010170311 | 8/2010 | | |
| JP | 2011092286 | 5/2011 | | |
| JP | 2016085715 | 5/2016 | | |
| JP | 2019074868 | 5/2019 | | |
| JP | 6664113 B2 * | 3/2020 | ............. | G16H 50/70 |
| KR | 20100065194 | 6/2010 | | |

OTHER PUBLICATIONS

"Written Opinion of the International Searching Authority (Form PCT/ISA/237) of PCT/JP2021/027869" mailed on Sep. 21, 2021, with English translation thereof, pp. 1-6.

"Office Action of Japan Counterpart Application", issued on Mar. 8, 2024, with English translation thereof, p. 1-p. 6.

* cited by examiner

IMAGE PROCESSING APPARATUS, IMAGE PROCESSING METHOD AND PROGRAM, AND IMAGE PROCESSING SYSTEM

CROSS-REFERENCE TO RELATED APPLICATIONS

The present application is a Continuation of PCT International Application No. PCT/JP2021/027869 filed on Jul. 28, 2021 claiming priority under 35 U.S.C § 119(a) to Japanese Patent Application No. 2020-148709 filed on Sep. 4, 2020. Each of the above applications is hereby expressly incorporated by reference, in its entirety, into the present application.

BACKGROUND OF THE INVENTION

1. Field of the Invention

The present invention relates to an image processing apparatus, an image processing method and program, and an image processing system, and more particularly to technology for image processing a medical image of an examination target.

2. Description of the Related Art

Computer-aided detection/diagnosis (CAD) for automatically detecting diseases from medical images is known. For CAD, a trained model that has been trained by deep learning, for example, is used. The utilization of CAD is expected to improve the work efficiency of radiologists and to prevent diseases from being overlooked.

Further, a pay-as-you-go billing system may be applied by using CAD as a cloud service. In this case, the fee is charged according to the processing executed by a user.

JP2016-85715A describes a diagnostic support service using cloud computing.

SUMMARY OF THE INVENTION

In a pay-as-you-go calculation processing system, it is important to increase the number of processes because the number of processes is directly connected to sales. However, in a system in which a user selects a process to be executed, the operation load of selecting a process to be executed from among a large number of processes is high, and it is assumed that the execution of the process may be postponed. Also, the user may forget the necessary processing. Furthermore, there is a likelihood that the user may overlook necessary processing not only in the pay-as-you-go system, but also in a fixed-rate system. Such problems are not limited to cloud services, but are the same for on-premises as well.

The present invention has been made in view of such circumstances, and an object thereof is to provide an image processing apparatus, an image processing method and program, and an image processing system that improve diagnostic accuracy by prompting processing requests more easily and without omission.

One aspect of the image processing apparatus for achieving the above object is an image processing apparatus comprising: at least one memory that stores instructions for execution by a processor; and at least one processor that executes the instructions stored in the memory, in which the processor is configured to: acquire image features of a medical image of an examination target; acquire a reference case and a diagnostic log based on the image features;

determine a recommended process for the medical image of the examination target based on the acquired reference case and diagnostic log; and present the recommended process.

According to the present aspect, the diagnostic accuracy can be improved by prompting processing requests more easily and without omission.

It is preferable that the recommended process includes at least one of an automatic lesion extraction process or an automatic disease name determination process for the medical image of the examination target. Accordingly, an appropriate process can be presented.

It is preferable that the processor is configured to acquire the reference case using at least one of digital imaging and communications in medicine (Dicom) tag information, position information, or similar image search. Accordingly, reference cases can be appropriately acquired.

It is preferable that the diagnostic log includes past diagnostic results managed for each user, and results of an influence of image processing on the diagnostic results. Accordingly, a recommended process can be appropriately determined.

It is preferable that the processor is configured to present a result of effective utilization of the recommended process in the reference case. Accordingly, a processing request can be appropriately prompted.

It is preferable that the processor is configured to additionally present a new recommended process based on a processing result of performing the recommended process. Accordingly, a recommended process can be more thoroughly presented without omission.

It is preferable that the processor is configured to acquire a past image similar to the medical image of the examination target based on the image features. Accordingly, a past image can be appropriately acquired.

One aspect of the image processing system for achieving the above object is an image processing system comprising: the above image processing apparatus; an imaging apparatus that captures a medical image of an examination target; a database that stores the reference case and the diagnostic log; and a display on which the recommended process is presented.

According to the present aspect, the diagnostic accuracy can be improved by prompting processing requests more easily and without omission.

It is preferable that the image processing apparatus is provided in a server device connected to the Internet. Accordingly, a plurality of users can access the image processing apparatus.

One aspect of the image processing method for achieving the above object is an image processing method comprising: an image feature acquisition step of acquiring image features of a medical image of an examination target; a similar image acquisition step of acquiring a past image and a diagnostic log similar to the medical image of the examination target based on the image features; a recommended process determination step of determining a recommended process for the medical image of the examination target based on the acquired past image and diagnostic log; and a presentation step of presenting the recommended process.

According to the present aspect, the diagnostic accuracy can be improved by prompting processing requests more easily and without omission.

One aspect of the program for achieving the above object is a program for causing a computer to execute the above image processing method. A computer-readable non-transitory storage medium in which the program is recorded may also be included in the present aspect.

According to the present aspect, the diagnostic accuracy can be improved by prompting processing requests more easily and without omission.

According to the aspects of the present invention, the diagnostic accuracy can be improved by prompting processing requests more easily and without omission.

DESCRIPTION OF THE PREFERRED EMBODIMENTS

Hereinafter, a preferred embodiment of the present invention will be described in detail with reference to the accompanying drawings.

[Overall Configuration of Medical Image Processing System]

Figure 1:
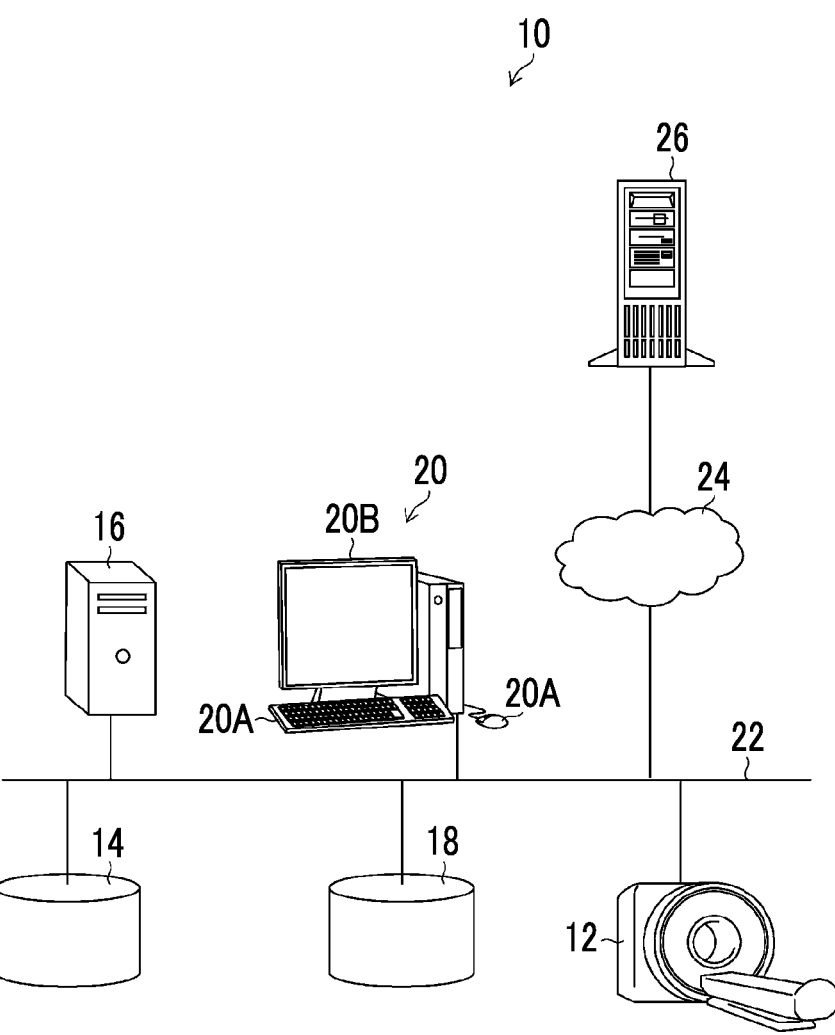
FIG. 1 is an overall configuration diagram of a medical image processing system 10.

FIG. 1 is an overall configuration diagram of a medical image processing system 10. The medical image processing system 10 is a system that captures an image of an examination target (patient) and presents a recommended process based on the captured image. As shown in FIG. 1, the medical image processing system 10 comprises medical image examination equipment 12, an image management unit 14, a recommended image processing determination processing unit 16, a diagnostic log management unit 18, a user terminal 20, and an image processing unit 26.

The medical image examination equipment 12, the image management unit 14, the recommended image processing determination processing unit 16, the diagnostic log management unit 18, and the user terminal 20 are provided in the medical institution and are connected to each other via an intra-hospital network 22 so that data can be transmitted and received.

A local area network (LAN) can be applied to the intra-hospital network 22. The intra-hospital network 22 may be wired or wireless.

The intra-hospital network 22 is connected to the Internet 24 via a router (not shown). The intra-hospital network 22 and the image processing unit 26 are connected to each other via the Internet 24 so that data can be transmitted and received.

The medical image examination equipment 12 is an imaging apparatus that captures an image of an examination target part of an examination target and generates a medical image. Examples of the medical image examination equipment 12 include an X-ray imaging apparatus, a computed tomography (CT) apparatus, a magnetic resonance imaging (MRI) apparatus, a positron emission tomography (PET) apparatus, an ultrasonic apparatus, and a computed radiography (CR) apparatus using a flat X-ray detector.

The image management unit 14 is a database that manages medical images captured by the medical image examination equipment 12. A computer having a large-capacity storage device can be applied to the image management unit 14. The computer is embedded with software that provides a function of a database management system.

The digital imaging and communications in medicine (Dicom) standard can be applied to the format of the medical image. Accessory information (Dicom tag information)

defined in the Dicom standard may be added to the medical image. Note that the term "image" in this specification can include the meaning of image data, which is a signal representing an image, in addition to the meaning of the image itself such as a photograph.

The recommended image processing determination processing unit 16 determines a recommended process for an image of an examination target. A personal computer or a workstation (an example of a computer) can be applied to the recommended image processing determination processing unit 16. The recommended image processing determination processing unit 16 comprises a processor 16A and a memory 16B. The processor 16A executes instructions stored in the memory 16B.

The hardware structure of the processor 16A is various processors as shown below. The various processors include a central processing unit (CPU) that is a general-purpose processor that acts as various functional units by executing software (programs), a programmable logic device (PLD) that is a processor whose circuit configuration can be changed after manufacture, such as a graphics processing unit (GPU) and a field programmable gate array (FPGA) which are processors specialized for image processing, a dedicated electrical circuit that is a processor having a circuit configuration designed exclusively for executing a specific process such as an application specific integrated circuit (ASIC), and the like.

One processing unit may be configured by one of the various processors, or may be configured by the same or different kinds of two or more processors (for example, a combination of a plurality of FPGAs, a combination of a CPU and an FPGA, or a combination of a CPU and a GPU). In addition, a plurality of functional units may be configured by one processor. As an example of configuring a plurality of functional units via one processor, first, as represented by a computer, such as a client or a server, there is a form in which one processor is configured by a combination of one or more CPUs and software, and this processor acts as a plurality of functional units. Second, as represented by a system on chip (SoC) or the like, there is a form of using a processor for realizing the function of the entire system including a plurality of functional units with one integrated circuit (IC) chip. Thus, various functional units are configured by using one or more of the above-described various processors as hardware structures.

Furthermore, the hardware structure of these various processors is, more specifically, an electrical circuit (circuitry) in which circuit elements such as semiconductor elements are combined.

The memory 16B stores instructions for execution by the processor 16A. The memory 16B includes a random access memory (RAM) and a read only memory (ROM) (not shown). The processor 16A uses the RAM as a work area, executes software using various programs and parameters including an image processing program stored in the ROM, and uses the parameters stored in the ROM or the like to execute various processes of the recommended image processing determination processing unit 16.

The diagnostic log management unit 18 is a database that manages diagnostic logs. A computer having a large-capacity storage device can be applied to the diagnostic log management unit 18. The computer is embedded with software that provides a function of a database management system. The image management unit 14 and the diagnostic log management unit 18 may be configured by one computer.

The user terminal 20 is terminal equipment used by a user such as a doctor. The user terminal 20 is, for example, a personal computer, and comprises an input device 20A and a display 20B. The user terminal 20 may be a workstation or a tablet terminal. A user inputs instructions to the medical image processing system 10 using the input device 20A. In addition, the recommended image processing determination processing unit 16 presents recommended image processing on the display 20B.

The image processing unit 26 (an example of an image processing apparatus) is configured by, for example, a server device. The image processing unit 26 performs image processing including at least one of an automatic lesion extraction process or an automatic disease name determination process on the medical image of the examination target. The image processing unit 26 can be accessed from the intrahospital networks 22 of a plurality of medical institutions via the Internet 24. The processing performed by the image processing unit 26 may be a billing system cloud service or a fixed-rate system cloud service.

[Medical Image Processing Method]

Figure 2:
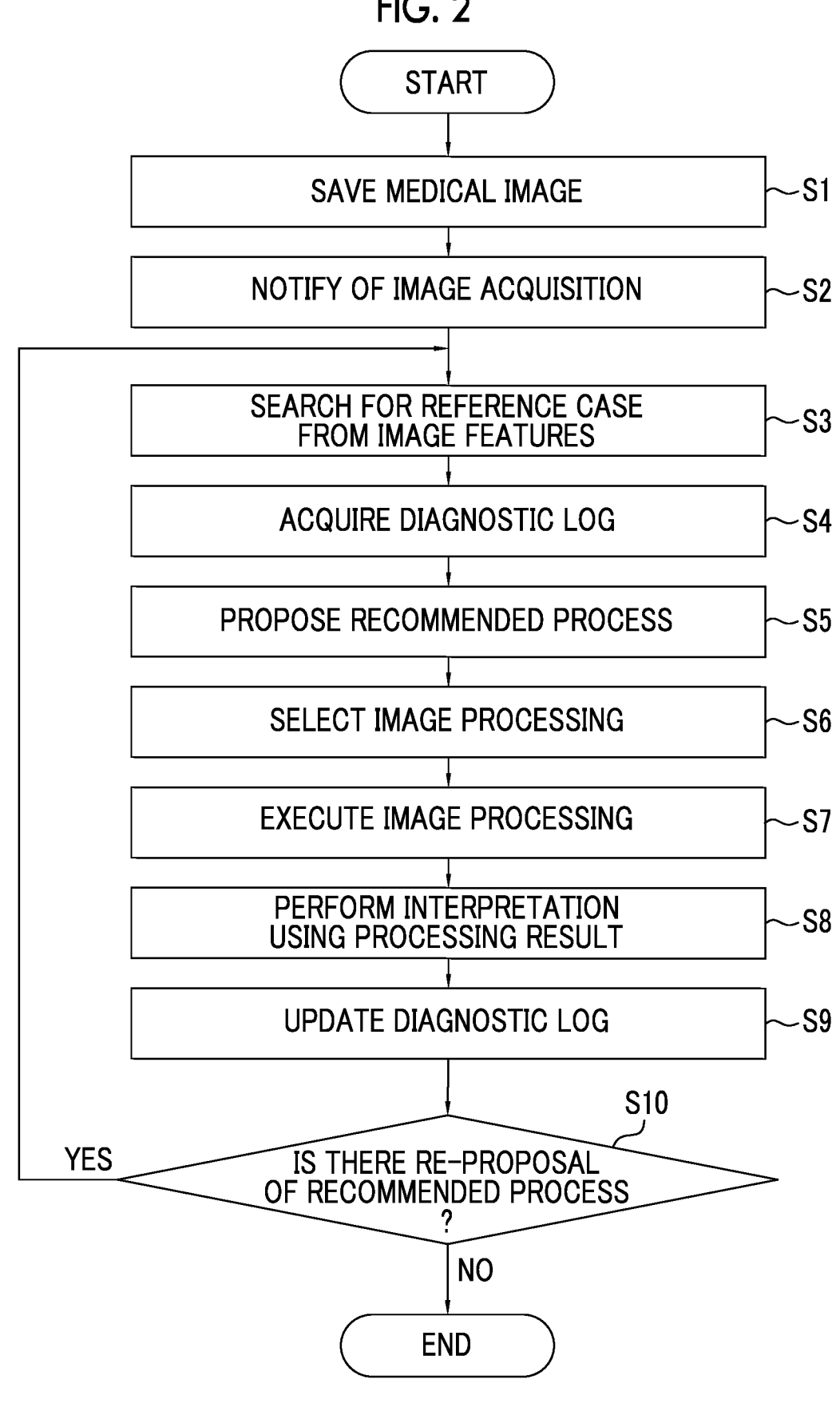
FIG. 2 is a flowchart showing each step of a medical image processing method.
Figure 3:
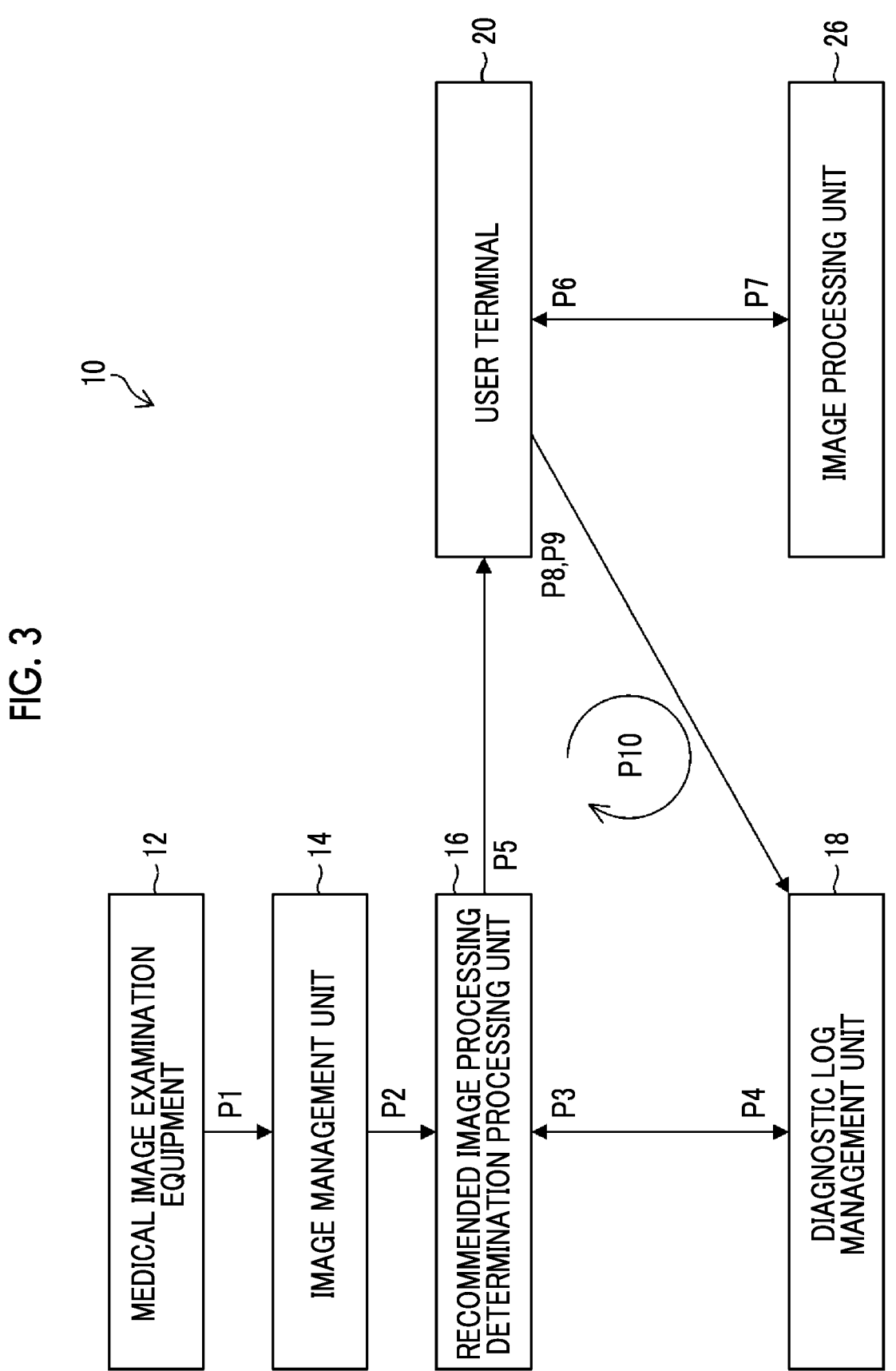
FIG. 3 is a process diagram showing each process of the medical image processing system.

FIG. 2 is a flowchart showing each step of a medical image processing method using the medical image processing system 10. FIG. 3 is a process diagram showing each process of the medical image processing system 10. Here, an example of presenting a user A with a recommended process for a medical image of a patient B who is an examination target will be described.

In Step S1, the medical image examination equipment 12 examines the patient B and saves the captured medical image in the image management unit 14 (process P1). For example, a CT examination is performed on the patient B in a case where a nodule is suspected (a case with a lung nodule near a blood vessel), and a CT image is captured. A CT apparatus (not shown) saves the captured CT image in the image management unit 14.

In Step S2, the image management unit 14 notifies the recommended image processing determination processing unit 16 that the medical image of the patient B has been input from the medical image examination equipment 12 (process P2). Here, the image management unit 14 notifies that the CT image of the patient B has been input.

In Step S3, the recommended image processing determination processing unit 16 acquires the image features of the medical image saved in Step S1 (process P1) (an example of an image feature acquisition step), and searches for similar past images and reference cases from the acquired image features (an example of a similar image acquisition step). For example, the recommended image processing determination processing unit 16 searches for and extracts a reference case that has been examined in the past using at least one of Dicom tag information, position information, or similar image search.

As an example using the Dicom tag information, the recommended image processing determination processing unit 16 can search for a similar case of multiple cases of lung nodules examined in the past from the multiple cases of lung nodules of an examination target.

The position information includes at least one of tag information such as the number of slices and a slice interval, or part information.

Further, similar image search is a technique of parameterizing image feature amounts and searching for similar images through parameter matching. That is, the recommended image processing determination processing unit 16 acquires a past image similar to the medical image of the patient B from the image management unit 14 based on the image features of the medical image.

Here, the recommended image processing determination processing unit 16 extracts a case (past examination target) having a lung nodule near a blood vessel like the patient B from the image features of the CT image of the patient B (process P3).

In Step S4 (an example of a similar image acquisition step), the recommended image processing determination processing unit 16 acquires the diagnostic log of the reference case extracted in Step S3 from the diagnostic log management unit 18 (process P4). The diagnostic log includes past diagnostic results (interpretation results) managed for each user, and results of the influence of image processing on the diagnostic results. The diagnostic result may include a diagnostic result before the user checks the CAD result and a diagnostic result after the user checks the CAD result. Moreover, the diagnostic result may be not for each user but for each hospital or the entire medical industry.

Here, it is assumed that the user A often overlooks diseases of lung nodules near blood vessels. The recommended image processing determination processing unit 16 acquires a diagnostic log indicating that the user A has found five overlooked points in the past images of the cases extracted in Step S3 by utilizing the lung CAD.

In Step S5, the recommended image processing determination processing unit 16 determines, as a recommended process, a process in which the processing result is effectively used from among the diagnostic logs acquired in Step S4 (an example of a recommended process determination step), and displays the recommended process on the display 20B of the user terminal 20 and makes a proposal (an example of presentation) to the user (an example of a presentation step). In addition, the recommended image processing determination processing unit 16 also displays the effectively utilized contents such as the interpretation time and the reduction of oversights (process P5).

Here, the recommended image processing determination processing unit 16 proposes the lung CAD to the user A as a recommended process. In addition, the recommended image processing determination processing unit 16 also displays additional detection at five locations as a result of the reduction of oversights.

In Step S6, the user A selects a recommended process to be executed. Here, the lung CAD presented in Step S5 is selected. Execution of the selected recommended process is requested from the user terminal 20 to the image processing unit 26 via the Internet 24 (process P6).

In Step S7, the image processing unit 26 executes the requested recommended process. Here, the image processing unit 26 executes lung CAD on the CT image captured in Step S1 (process P7). A result of the recommended process executed by the image processing unit 26 is transmitted to the user terminal 20.

In Step S8, the user A performs interpretation utilizing the result of the recommended process in Step S7 on the display 20B of the user terminal 20. Here, after the user A independently interprets the lung nodule, he or she refers to the results of lung CAD, which is the recommended process, to check for any oversights, and completes the interpretation (process P8). The user A uses the input device 20A of the user terminal 20 to input the result of interpretation as a diagnostic result.

In Step S9, the user terminal 20 saves the diagnostic result input by the user A in Step S8 in the diagnostic log management unit 18. Here, the user terminal 20 updates the diagnostic log in which a serious nodule (some of the overlooked ones were found this time) is checked.

In Step S10, the recommended image processing determination processing unit 16 determines whether or not to re-propose the recommended process. In a case where the recommended process is to be re-proposed, the recommended image processing determination processing unit 16 returns to Step S3 and repeats the processes of Steps S3 to S9 (process P10). Here, the recommended image processing determination processing unit 16 uses the updated diagnostic log to search for reference cases again. For example, in a case where there is a serious nodule, the recommended image processing determination processing unit 16 proposes bone metastasis CAD as a recommended process because bone metastasis may be overlooked. In a case where the recommended process is not re-proposed, the medical image processing system 10 ends the process of this flowchart.

As described above, according to the present aspect, the diagnostic accuracy can be improved by prompting processing requests more easily and without omission. In addition, in a case where the image processing unit 26 is a billing system, it is possible to promote the use of the system.

At least Steps S3, S4, and S5, which are processed by the recommended image processing determination processing unit 16, constitute the image processing method according to the present embodiment. An image processing program for causing a computer to execute the image processing method is stored in a ROM (not shown) of the memory 16B of the recommended image processing determination processing unit 16.

[Other]

The technical scope of the present invention is not limited to the scope described in the above embodiment. The configurations and the like in each embodiment can be appropriately combined between the embodiments without departing from the spirit of the present invention.

EXPLANATION OF REFERENCES

10: medical image processing system
12: medical image examination equipment
14: image management unit
16: recommended image processing determination processing unit
18: diagnostic log management unit
20: user terminal
22: intra-hospital network
24: Internet
26: image processing unit
S1 to S10: each step of medical image processing method

What is claimed is:

1. An image processing apparatus comprising:
at least one memory that stores instructions for execution by a processor; and
at least one processor that executes the instructions stored in the memory,
wherein the processor is configured to:
acquire image features of a medical image of an examination target;
acquire a reference case based on the image features and a diagnostic log associated with the reference case, wherein the diagnostic log includes past diagnostic results managed for each user and results of an influence of image processing on the past diagnostic results, wherein the past diagnostic results comprise at least a diagnostic result before a user checks a result of the image processing and a diagnostic result after the user checks the result of the image processing;
determine a recommended process for the medical image of the examination target based on the acquired reference case and the results of the influence of the image processing on the past diagnostic results as indicated in the diagnostic log; and
display the recommended process on a display of a user terminal.

2. The image processing apparatus according to claim 1, wherein the recommended process includes at least one of an automatic lesion extraction process or an automatic disease name determination process for the medical image of the examination target.

3. The image processing apparatus according to claim 1, wherein the processor is configured to acquire the reference case using at least one of digital imaging and communications in medicine (Dicom) tag information, position information, or similar image search.

4. The image processing apparatus according to claim 1, wherein the processor is configured to present a result of effective utilization of the recommended process in the reference case.

5. The image processing apparatus according to claim 1, wherein the processor is configured to additionally present a new recommended process based on a processing result of performing the recommended process.

6. The image processing apparatus according to claim 1, wherein the processor is configured to acquire a past image similar to the medical image of the examination target based on the image features.

7. An image processing system comprising:
the image processing apparatus according to claim 1;
an imaging apparatus that captures a medical image of an examination target;
a database that stores the reference case and the diagnostic log; and
the display on which the recommended process is presented.

8. The image processing system according to claim 7, wherein the image processing apparatus is provided in a server device connected to the Internet.

9. An image processing method comprising:
an image feature acquisition step of acquiring image features of a medical image of an examination target;
a similar image acquisition step of acquiring a past image similar to the medical image of the examination target based on the image features and a diagnostic log associated with the past image, wherein the diagnostic log includes past diagnostic results managed for each user and results of an influence of image processing on the past diagnostic results, wherein the past diagnostic results comprise at least a diagnostic result before a user checks a result of the image processing and a diagnostic result after the user checks the result of the image processing;
a recommended process determination step of determining a recommended process for the medical image of the examination target based on the acquired past image and the results of the influence of the image processing on the past diagnostic results as indicated in the diagnostic log; and
a presentation step of displaying the recommended process on a display of a user terminal.

10. A non-transitory, computer-readable tangible recording medium which records thereon a program for causing, when read by a computer, the computer to execute the image processing method according to claim 9.

* * * * *